US012692489B2

(12) United States Patent
Zhao

(10) Patent No.: US 12,692,489 B2
(45) Date of Patent: Jul. 28, 2026

(54) MAGNETIC BEAD SUSPENSION REAGENT, METHOD FOR PURIFYING NUCLEIC ACID AND METHOD FOR SORTING NUCLEIC ACID

(71) Applicants: BEIJING BOE TECHNOLOGY DEVELOPMENT CO., LTD., Beijing (CN); BOE TECHNOLOGY GROUP CO., LTD., Beijing (CN)

(72) Inventor: Zijian Zhao, Beijing (CN)

(73) Assignees: BEIJING BOE TECHNOLOGY DEVELOPMENT CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 156 days.

(21) Appl. No.: 17/778,852

(22) PCT Filed: Jun. 4, 2021

(86) PCT No.: PCT/CN2021/098324
§ 371 (c)(1),
(2) Date: Dec. 8, 2022

(87) PCT Pub. No.: WO2022/252212
PCT Pub. Date: Dec. 8, 2022

(65) Prior Publication Data
US 2024/0158777 A1 May 16, 2024

(51) Int. Cl.
*C12N 15/10* (2006.01)
*C12Q 1/6806* (2018.01)

(52) U.S. Cl.
CPC ....... *C12N 15/1013* (2013.01); *C12Q 1/6806* (2013.01)

(58) Field of Classification Search
None
See application file for complete search history.

(56) References Cited

U.S. PATENT DOCUMENTS

2017/0121705 A1 5/2017 Goldrick et al.
2020/0080074 A1 3/2020 Stroeder et al.

FOREIGN PATENT DOCUMENTS

| CN | 101613697 | A | 12/2009 | | |
|---|---|---|---|---|---|
| CN | 101935646 | A | 1/2011 | | |
| CN | 105695450 | A | 6/2016 | | |
| CN | 108192891 | A | 6/2018 | | |
| CN | 109022417 | A | 12/2018 | | |
| CN | 109055363 | A | 12/2018 | | |
| CN | 109735532 | * | 5/2019 | ............ | C12N 15/10 |
| CN | 109735532 | A | 5/2019 | | |
| CN | 109750030 | A | 5/2019 | | |
| CN | 110088282 | A | 8/2019 | | |
| CN | 110283818 | A | 9/2019 | | |
| CN | 111197043 | A | 5/2020 | | |
| CN | 112226489 | A | 1/2021 | | |
| CN | 112391381 | A | 2/2021 | | |
| CN | 116355893 | A | 6/2023 | | |
| WO | 2021055084 | A1 | 3/2021 | | |

OTHER PUBLICATIONS

"Unfolding and Refolding of Protein by a Combination of Ionic and Nonionic Surfactants", Saha et al., ACS Omega (2018), 3(7), 8260-8270.*

Lever, Mark A., et al., "A modular method for the extraction of DNA and RNA, and the separation of DNA pools from diverse environmental sample types", frontiers in Microbiology, Methods, May 19, 2015, 25 pages.

First Office Action of Chinese Patent Application No. 202180001410.6 (Foreign Text, 9 Pages, English Translation Thereof, 9 Pages) (Dec. 13, 2024).

Li et al. "Research progress on nucleic acid extraction methods" China Animal Health Inspection 28(12):75-78 (2011).

Organic Chemistry, 2nd Edition, Nitsmizarin ed., Metallurgical Industry Press, 1st Edition (Jan. 31, 2014).

* cited by examiner

*Primary Examiner* — Ann Montgomery
(74) *Attorney, Agent, or Firm* — Myers Bigel, P.A.

(57) ABSTRACT

The present disclosure provides a magnetic bead suspension reagent, a method for purifying nucleic acid by using the magnetic bead suspension reagent, and a method for sorting nucleic acid by using the magnetic bead suspension reagent. The magnetic bead suspension reagent includes magnetic beads and a surfactant, the surfactant includes a nonionic surfactant and an anionic/cationic surfactant, and both the nonionic surfactant and the anionic/cationic surfactant are present in the magnetic bead suspension reagent.

12 Claims, 4 Drawing Sheets

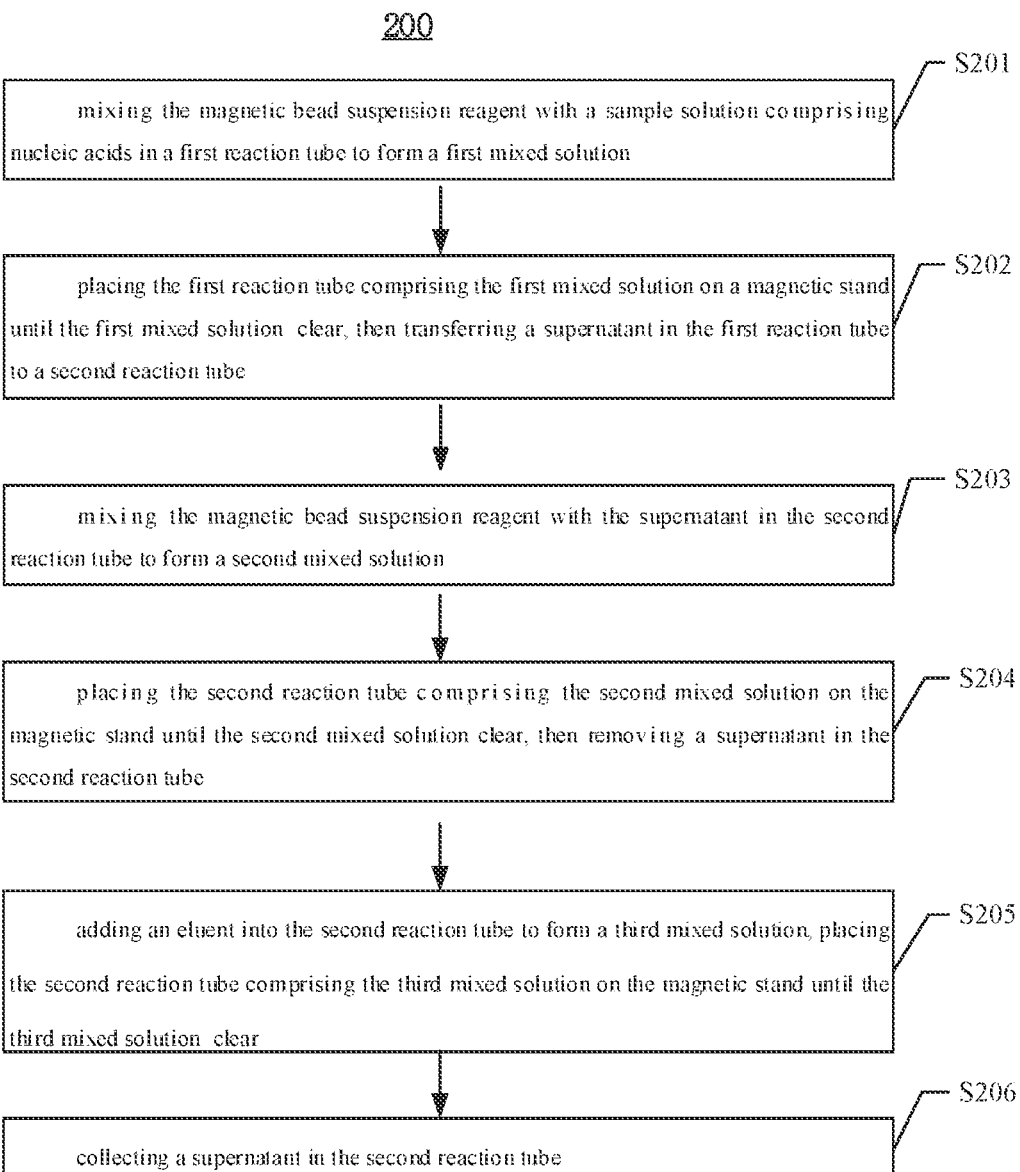

_200_

┌─ S201
mixing the magnetic bead suspension reagent with a sample solution comprising nucleic acids in a first reaction tube to form a first mixed solution ┌─ S202
placing the first reaction tube comprising the first mixed solution on a magnetic stand until the first mixed solution clear, then transferring a supernatant in the first reaction tube to a second reaction tube ┌─ S203
mixing the magnetic bead suspension reagent with the supernatant in the second reaction tube to form a second mixed solution ┌─ S204
placing the second reaction tube comprising the second mixed solution on the magnetic stand until the second mixed solution clear, then removing a supernatant in the second reaction tube ┌─ S205
adding an eluent into the second reaction tube to form a third mixed solution, placing the second reaction tube comprising the third mixed solution on the magnetic stand until the third mixed solution clear ┌─ S206
collecting a supernatant in the second reaction tube

FIG. 4

MAGNETIC BEAD SUSPENSION REAGENT, METHOD FOR PURIFYING NUCLEIC ACID AND METHOD FOR SORTING NUCLEIC ACID

RELATED APPLICATIONS

The present application is a 35 U.S.C. 371 national stage application of PCT International Application No. PCT/CN2021/098324 filed on Jun. 4, 2021, the entire disclosure of which is incorporated herein by reference.

TECHNICAL FIELD

The present disclosure relates to the technical field of biomedicine, and in particular, to a magnetic bead suspension reagent, a method for purifying nucleic acid and a method for sorting nucleic acid by using the magnetic bead suspension reagent.

BACKGROUND

Polymerase Chain Reaction (PCR) is a molecular biology technique used to amplify specific nucleic acid fragments, which can replicate a small amount of deoxyribonucleic acid (DNA) or ribonucleic acid (RNA) in large quantities, greatly increasing their number. Precision medical technologies such as PCR and gene sequencing are increasingly recognized by the medical community, providing new ideas and methods for digital medicine. The leap-forward development of PCR technology and gene sequencing technology can realize a further depth diagnosis of diseases at the molecular level, and its application in the field of medicine has been further expanded.

SUMMARY

According to an aspect of the present disclosure, there is provided a magnetic bead suspension reagent comprising magnetic beads and a surfactant, the surfactant comprises a nonionic surfactant and an anionic/cationic surfactant, and both the nonionic surfactant and the anionic/cationic surfactant are present in the magnetic bead suspension reagent.

In some embodiments, a side chain of the anionic/cationic surfactant comprises a carbon chain, and a length of the carbon chain is greater than or equal to 10 carbon atoms and less than or equal to 20 carbon atoms.

In some embodiments, the surfactant is selected from a group consisting of Tween 20, polyethylene glycol octyl phenyl ether, sodium dodecyl sulfate, octadecyl diester quaternary ammonium salt.

In some embodiments, the surfactant comprises Tween 20, sodium dodecyl sulfate and octadecyl diester quaternary ammonium salt.

In some embodiments, the magnetic bead suspension reagent further comprises a dehydrating agent and an ionic salt. A volume of the surfactant accounts for 0.5%~5% of a volume of the magnetic bead suspension reagent, a mass of the dehydrating agent accounts for 20%~30% of a mass of the magnetic bead suspension reagent, and a molarity of the ionic salt in the magnetic bead suspension reagent is 1 mol/L~5 mol/L.

In some embodiments, the volume of the surfactant accounts for 0.5% of the volume of the magnetic bead suspension reagent, the mass of the dehydrating agent accounts for 30% of the mass of the magnetic bead suspension reagent, and the molarity of the ionic salt in the magnetic bead suspension reagent is 1.5 mol/L.

In some embodiments, the dehydrating agent comprises polyethylene glycol with at least one relative molecular mass, and the relative molecular mass of the polyethylene glycol is in a range of 8000~15000.

In some embodiments, the ionic salt is selected from a group consisting of NaCl and $MgCl_2$.

In some embodiments, the magnetic bead suspension reagent further comprises a buffer solution. The buffer solution comprises tris(hydroxymethyl)aminomethane hydrochloride, and a molarity of the buffer solution is 0.1 mmol/L~10 mmol/L, and a pH value of the buffer solution is 7.5~8.5.

In some embodiments, the magnetic bead suspension reagent further comprises a stabilizing solution, the stabilizing solution comprises ethylene diamine tetraacetic acid, and a molarity of the stabilizing solution is 0.5 mmol/L~20 mmol/L.

In some embodiments, each of the magnetic beads is a superparamagnetic magnetic bead, and the superparamagnetic magnetic bead has a three-layer structure, an innermost layer of the three-layer structure is polystyrene, an intermediate layer of the three-layer structure is $Fe_3O_4$, and an outermost layer of the three-layer structure is a modified layer with carboxyl and/or silanol functional groups.

In some embodiments, a ratio of a mass of the intermediate layer of the magnetic bead to a mass of the magnetic bead is greater than 70%, and a particle size of the magnetic bead is 50 nm~4.5 μm, and a concentration of the magnetic beads in the magnetic bead suspension reagent is 1-10 mg/mL.

According to another aspect of the present disclosure, there is provided a method for purifying nucleic acids, the method comprises: mixing the magnetic bead suspension reagent described in any of the foregoing embodiments with a sample solution comprising nucleic acids in a reaction tube to form a first mixed solution; placing the reaction tube accommodating the first mixed solution on a magnetic stand until the first mixed solution clear, and then removing a supernatant in the reaction tube; adding an eluent into the reaction tube to form a second mixed solution, placing the reaction tube accommodating the second mixed solution on the magnetic stand until the second mixed solution clear; and collecting a supernatant in the reaction tube.

In some embodiments, after the step of removing a supernatant in the reaction tube and before the step of adding an eluent into the reaction tube to form a second mixed solution, the method further comprises performing the following step at least once: adding an ethanol solution into the remaining solution in the reaction tube to form a third mixed solution, letting the third mixed solution stand until the third mixed solution clear, and then removing the supernatant comprising the ethanol solution.

In some embodiments, the step of adding an eluent into the reaction tube to form a second mixed solution, placing the reaction tube accommodating the second mixed solution on the magnetic stand until the second mixed solution clear comprises: taking the reaction tube out from the magnetic stand, adding Te buffer solution into the reaction tube at a ratio of 2 times the volume of the sample solution to form the second mixed solution, and then placing the reaction tube accommodating the second mixed solution on the magnetic stand, letting the second mixed solution stand until the second mixed solution clear.

According to yet another aspect of the present disclosure, there is provided a method for sorting nucleic acids, the method comprises: mixing the magnetic bead suspension reagent described in any of the foregoing embodiments with a sample solution comprising nucleic acids in a first reaction tube to form a first mixed solution; placing the first reaction tube accommodating the first mixed solution on a magnetic stand until the first mixed solution clear, and then transferring a supernatant in the first reaction tube into a second reaction tube; mixing the magnetic bead suspension reagent described in any of the foregoing embodiments with the supernatant in the second reaction tube to form a second mixed solution; placing the second reaction tube accommodating the second mixed solution on the magnetic stand until the second mixed solution clear, and then removing a supernatant in the second reaction tube; adding an eluent into the second reaction tube to form a third mixed solution, and placing the second reaction tube accommodating the third mixed solution on the magnetic stand until the third mixed solution clear; and collecting a supernatant in the second reaction tube.

In some embodiments, the step of placing the first reaction tube accommodating the first mixed solution on a magnetic stand until the first mixed solution clear, and then transferring a supernatant in the first reaction tube into a second reaction tube comprises: placing the first reaction tube accommodating the first mixed solution on the magnetic stand and letting the first mixed solution stand until the first mixed solution clear, so that the magnetic beads move to the bottom of the first reaction tube and adsorb nucleic acids with a first length, and then transferring the supernatant comprising nucleic acids with a second length and nucleic acids with a third length in the first reaction tube into the second reaction tube. The first length is greater than the second length and the third length.

In some embodiments, the step of placing the second reaction tube accommodating the second mixed solution on the magnetic stand until the second mixed solution clear, and then removing a supernatant in the second reaction tube comprises: placing the second reaction tube accommodating the second mixed solution on the magnetic stand and letting the second mixed solution stand until the second mixed solution clear, so that the magnetic beads move to the bottom of the second reaction tube and adsorb the nucleic acids with the second length, and then removing the supernatant comprising the nucleic acids with the third length in the second reaction tube. The second length is greater than the third length.

In some embodiments, the step of collecting a supernatant in the second reaction tube comprises: collecting the supernatant in the second reaction tube to obtain the nucleic acids with the second length.

In some embodiments, after the step of removing a supernatant in the second reaction tube and before the step of adding an eluent into the second reaction tube to form a third mixed solution, the method further comprises performing the following step at least once: adding an ethanol solution into the remaining solution in the second reaction tube to form a fourth mixed solution, letting the fourth mixed solution stand until the fourth mixed solution clear, and then removing the supernatant comprising the ethanol solution.

In some embodiments, the step of adding an eluent into the second reaction tube to form a third mixed solution, and placing the second reaction tube accommodating the third mixed solution on the magnetic stand until the third mixed solution clear comprises: taking the second reaction tube out from the magnetic stand, adding Te buffer solution into the second reaction tube at a ratio of 2 times the volume of the sample solution to form the third mixed solution, then placing the second reaction tube accommodating the third mixed solution on the magnetic stand and letting the third mixed solution stand until the third mixed solution clear.

BRIEF DESCRIPTION OF THE DRAWINGS

In order to describe the technical solutions in the embodiments of the present disclosure more clearly, the accompanying drawings required in the embodiments will be briefly introduced below. Obviously, the drawings in the following description are only some embodiments of the present disclosure. For those of ordinary skill in the art, other drawings can also be obtained based on these drawings without any creative effort.

FIG. 4 illustrates a flowchart of a method for sorting nucleic acids using a magnetic bead suspension reagent provided according to an embodiment of the present disclosure.

DETAILED DESCRIPTION OF THE DISCLOSURE

Figure 1:
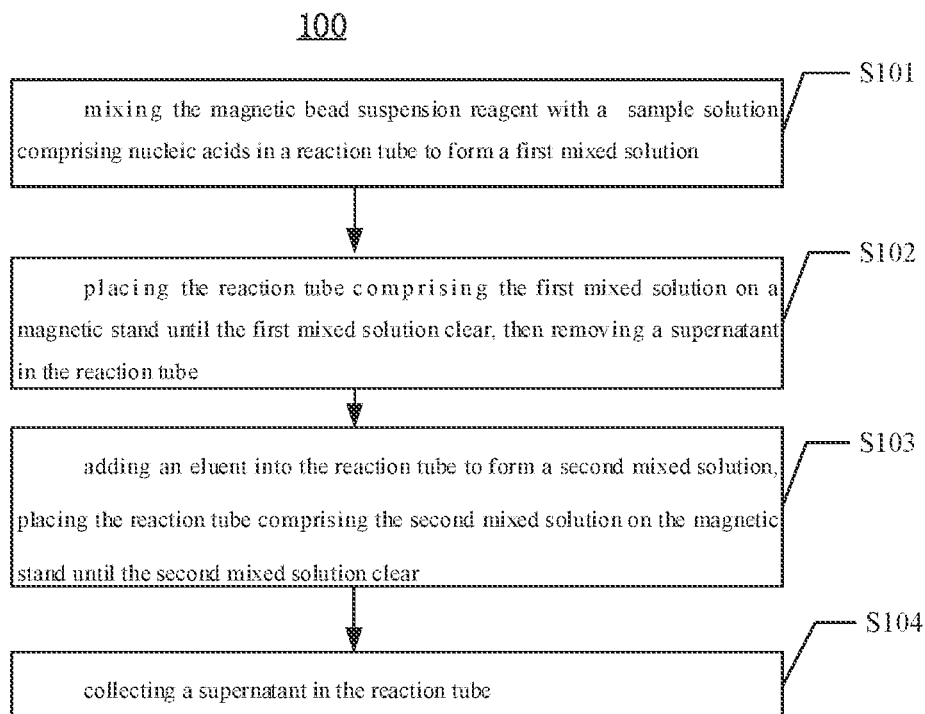
FIG. 1 illustrates a flowchart of a method for purifying nucleic acids using a magnetic bead suspension reagent provided according to an embodiment of the present disclosure.

The technical solutions in the embodiments of the present disclosure will be clearly and completely described below with reference to the accompanying drawings in the embodiments of the present disclosure. Obviously, the described embodiments are only some, but not all, embodiments of the present disclosure. Based on the embodiments in the present disclosure, all other embodiments obtained by those of ordinary skill in the art without creative efforts shall fall within the protection scope of the present disclosure.

Before formally describing the technical solutions of the embodiments of the present disclosure, the terms used in the embodiments of the present disclosure are explained and defined as follows to help those skilled in the art to understand the technical solutions of the embodiments of the present disclosure more clearly.

As used herein, the term "nucleic acid" is a general term for deoxyribonucleic acid (DNA) and ribonucleic acid (RNA), which is a biological macromolecular compound composed of many nucleotide monomers and is one of the most basic substances of life. Nucleic acid is a kind of biopolymer, which is an indispensable component of all known life forms and is the most important substance in all biological molecules, and widely exists in all animal and plant cells and microorganisms. Nucleic acid is composed of nucleotides, and a nucleotide monomer is composed of five-carbon sugars, phosphate groups, and nitrogenous bases. Where the five-carbon sugar is ribose, the resulted polymer is RNA. Where the five-carbon sugar is deoxyribose, the resulted polymer is DNA.

As used herein, the term "Polymerase Chain Reaction (PCR)" is a biological technique which is used to amplify specific nucleic acid molecules. Taking DNA molecules as an example, the basic principle of PCR is that DNA can be denatured and melted into single chain at high temperature (such as around 95° C.). When the temperature drops to a low temperature (for example, about 60° C.), the primer and the single chain combine to become double chains again according to the principle of base complementary pairing. Therefore, by controlling the denaturation and renaturation of DNA by temperature changes, and adding designed primers, a large number of DNA replication can be achieved. PCR reactions comprise but are not limited to digital PCR (dPCR), quantitative PCR, and real-time PCR. DPCR technology can provide quantitative analysis technology for digitizing DNA quantitative information, which can further improve the sensitivity and accuracy of the detection.

As used herein, the term "magnetic bead" refers to a particle having the magnetic property, such as a nanoparticle having the magnetic property. The magnetic bead may be superparamagnetic magnetic bead. Superparamagnetic magnetic bead has the following properties: when there is no external magnetic field, the magnetic bead has no magnetism and is evenly suspended in the solution; when an external magnetic field is applied, the magnetic bead is magnetic and can be separated from the solution. The surface of the magnetic bead is usually connected with active substances such as biologically active adsorbents or other ligands, which can achieve specific binding or dissociation with specific biomolecules or cells under the action of an external magnetic field. The magnetic bead separates the target nucleic acids in the sample solution from the impurities in the solution through the principle that the active group of the magnetic particle can bind and dissociate with the nucleic acid under certain conditions, so that the purification of the target nucleic acids can be realized. The magnetic bead can realize high-throughput automation of nucleic acid samples, and is widely used in the fields of gene sequencing and molecular diagnosis.

As used herein, the term "particle size of the magnetic bead" refers to the size of the magnetic bead, i.e., the length of the magnetic bead in a certain direction. For example, when the shape of the magnetic bead is spherical, the term "particle size of the magnetic bead" refers to the diameter of the magnetic bead. When the shape of the magnetic bead is rod, the term "particle size of the magnetic bead" refers to the length of the magnetic bead in the direction of the shorter side.

The separation and purification of cells and various life macromolecules such as nucleic acids, proteins and polypeptides are indispensable links in various research fields of life sciences. Separation and purification technology plays a very important role in the development of life sciences. Nucleic acids are greatly increased in quantity by PCR technology. Generally speaking, the crude extract of nucleic acid (DNA and/or RNA) obtained by centrifugation after cell lysis cannot be directly used for analysis, and needs to be purified to obtain a higher-purity extract. Traditional purification methods are mostly based on chromatography and centrifugal sedimentation, but this traditional method requires chromatography columns, toxic reagents (such as phenol) and expensive centrifuges, and has disadvantages such as time-consuming, labor-intensive, expensive, unfavorable to simplify the operation, and unfriendly to the environment, etc. Compared with traditional methods, the use of magnetic particles to purify target nucleic acids in the sample solution has great advantages: firstly, the separation method using magnetic particles can greatly reduce the dependence on centrifuges or even eliminate the need for centrifuges; secondly, the method of separation by magnetic particles is easy to operate, and even all operations can be performed in a single centrifuge tube; thirdly, the method of separation by magnetic particles eases the operation, which is beneficial to ensure the integrity of DNA/RNA molecules.

The magnetic bead suspension reagent usually comprises magnetic beads, dehydrating agents, ionic salts, surfactants and other compositions, and the price of magnetic beads is usually very expensive. The main principle of nucleic acid purification using magnetic bead suspension reagent is based on the solid phase reversible immobilization (SPRI) method. When the sample solution comprising nucleic acid molecules is mixed with the magnetic bead suspension reagent, the nucleic acid molecule is dehydrated in a high concentration of dehydrating agent and ionic salt (such as NaCl), and the molecular conformation is compressed from linear to curled sphere and exposes a large number of phosphate groups with negative charge. The negatively charged phosphate group and the carboxyl functional group on the outermost layer of the magnetic bead form an "electric bridge" under the action of Nat, so that nucleic acid molecules are specifically adsorbed to the surface of the magnetic bead. After the dehydrating agent and ionic salt are removed (and the impurities in the sample solution are also removed), aqueous molecules are added to the remaining solution, and the nucleic acid molecules are quickly and fully hydrated, thereby removing the ion interaction among nucleic acid molecules, magnetic beads and salt ions, and the nucleic acid molecules adsorbed to the magnetic beads are dissociated from the surfaces of the magnetic beads. These nucleic acid molecules are collected, thereby realizing the purification of nucleic acids.

The types of components comprised in the magnetic bead suspension reagent, the ratios among the components, and the specific compositions of each component have a very important influence on the performance of the magnetic bead suspension reagent. The inventors of the present application have found that, in the conventional technical solution, the surfactant in the magnetic bead suspension reagent is either only a nonionic surfactant or only an anionic/cationic surfactant. However, the single use of nonionic surfactant does not promote the formation of "electric bridge", which requires a higher concentration of salt ions and a larger amount of magnetic beads. The price of magnetic beads is very expensive, so this significantly increases the cost. Although the single use of the anionic/cationic surfactant is beneficial to promote the formation of "electric bridge", it seriously affects the dehydration process of nucleic acid and is not favorable to nucleic acid purification.

In view of the above situations, embodiments of the present disclosure provide a magnetic bead suspension reagent comprising magnetic beads and a surfactant, the surfactant comprises a nonionic surfactant and an anionic/cationic surfactant, and both the nonionic surfactant and the anionic/cationic surfactant are present in the magnetic bead suspension reagent.

In the magnetic bead suspension reagent, the dehydrating agent (such as polyethylene glycol) is used to dehydrate nucleic acid (such as DNA and/or RNA) molecules and expose a large number of negatively charged phosphate groups, thereby making nucleic acid molecules negatively charged, and magnetic beads are also negatively charged. Therefore, in order to enable the adsorption of nucleic acid molecules to the surface of magnetic beads for purification or sorting, the presence of cations (such as $Na^+$ or $Mg_{2+}$ in ionic salts) is required in the magnetic bead suspension reagent, so that, under the action of the cation, the negatively charged phosphate group of the nucleic acid molecule forms an "electric bridge" with the carboxyl functional group on the outermost layer of the magnetic bead, such that the nucleic acid molecule is specifically adsorbed to the surface of the magnetic bead. Although the presence of ionic salts is required in the magnetic bead suspension reagent, the ionic salts need to be kept in an appropriate concentration range, because when purifying or sorting nucleic acid molecules, the ionic salts need to be diluted, and the relationship between the diluted ionic salt concentration and purification efficiency or sorting efficiency is similar to an "S"-shaped curve (the abscissa is the concentration of ionic salts, and the ordinate is the purification efficiency or sorting efficiency). Too high or too low concentration of ionic salts is not favorable to the improvement of purification efficiency or sorting efficiency. Only when the concentration of ionic salts is in the appropriate middle range can significantly improve the purification efficiency or sorting efficiency. Therefore, only if the ionic salts are kept in a suitable concentration range, they can be rapidly diluted to the "optimal concentration range" during the purification or sorting process, thereby significantly improving the purification or sorting efficiency. In addition, magnetic beads are usually in the micrometer scale, so they are very easy to agglomerate, thus surfactants are required to uniformly disperse the magnetic beads in the reagent. In view of the above reasons, the nonionic surfactant and the anionic/cationic surfactants are all present in the surfactant of the magnetic bead suspension reagent provided in the embodiments of the present disclosure. On the one hand, the nonionic surfactant can be used to maintain the dispersion of magnetic beads; on the other hand, the anions/cations in the surfactant can be used to promote ionization to supplement the ionic salt in the reagent, so that the concentration of the ionic salts in the reagent can be quickly diluted to the "optimal concentration range", so as to achieve rapid purification or sorting. Moreover, anionic/cationic surfactants can also be relied on to promote the formation of "electric bridge", thereby promoting the adsorption efficiency of nucleic acids by magnetic beads. Therefore, the magnetic bead suspension reagent provided in the embodiments of the present disclosure can not only reduce the amount of magnetic beads and thus greatly reduce the cost, but also improve the purification and sorting efficiency of nucleic acids.

In some embodiments, the side chain of the anionic/cationic surfactant in the surfactant comprises a carbon chain, a length of the carbon chain is greater than or equal to 10 carbon atoms and less than or equal to 20 carbon atoms. By way of example only but not limitation, the anionic surfactant may be sodium dodecyl sulfate (SDS) and the cationic surfactant may be octadecyl diester quaternary ammonium salt. The carbon chain in anionic/cationic surfactant is hydrophobic, and sulfate or quaternary ammonium salt is hydrophilic. If the length of the carbon chain is less than 10 carbon atoms, the surfactant will have poor surface activity and be easily dissolved in the reagent; if the length of the carbon chain is greater than 20 carbon atoms, the surfactant will have poor emulsification, and be prone to precipitation in the reagent. Therefore, 10-20 carbon atoms is the optimal carbon chain length, which makes the surfactant have better surface activity and better emulsification. In addition, the sulfate or quaternary ammonium salt has a suitable amount of charge compared to, for example, phosphate, so that the surfactant can have better emulsification effect and stability.

In some embodiments, the surfactant is selected from a group consisting of Tween 20, polyethylene glycol octyl phenyl ether (Triton X-100), sodium dodecyl sulfate (SDS), octadecyl diester quaternary ammonium salt, so that the surfactant comprises both the nonionic surfactant and the anionic/cationic surfactant. Tween 20 and polyethylene glycol octyl phenyl ether are nonionic surfactants, sodium dodecyl sulfate is an anionic surfactant, and octadecyl diester quaternary ammonium salt is a cationic surfactant. In an example, the surfactant may comprise Tween 20, sodium dodecyl sulfate, and octadecyl diester quaternary ammonium salt. For example, the volume of Tween 20 can be 0.5% of the volume of the magnetic bead suspension reagent, the volume of sodium dodecyl sulfate can be 0.5% of the volume of the magnetic bead suspension reagent, the volume of octadecyl diester quaternary ammonium salt can be 0.5% of the volume of the magnetic bead suspension reagent. In another example, the surfactant may comprise polyethylene glycol octyl phenyl ether, sodium dodecyl sulfate, and octadecyl diester quaternary ammonium salt. In yet another example, the surfactant may comprise Tween 20, polyethylene glycol octyl phenyl ether, sodium dodecyl sulfate, and octadecyl diester quaternary ammonium salt.

In addition to the magnetic beads and the surfactant, the magnetic bead suspension reagent also comprises a dehydrating agent and an ionic salt. The dehydrating agent may be polyethylene glycol (PEG) with at least one relative molecular mass, and the relative molecular mass of the polyethylene glycol is in the range of 8000-15000. For example, the relative molecular mass of polyethylene glycol can be any appropriate value such as 8000, 9000, 10000, 11000, 12000, 13000, 14000, 15000 and the like. The combination of surfactant and polyethylene glycol with appropriate relative molecular mass can form a better dehydration-bridge forming system, thereby further improving the adsorption efficiency of nucleic acids by magnetic beads, which is favorable to improve the purification and sorting effect of nucleic acids. It should be noted that the phrase "the dehydrating agent may be polyethylene glycol with at least one relative molecular mass" means that the dehydrating agent may be polyethylene glycol with a single relative molecular mass, or it may be a mixture of polyethylene glycols with different relative molecular mass. For example, in an example, the dehydrating agent is polyethylene glycol with a relative molecular mass of 8000. In another example, the dehydrating agent is a mixture of polyethylene glycol with a relative molecular mass of 8,000 and polyethylene glycol with a relative molecular mass of 10,000. In yet another example, the dehydrating agent is a mixture of polyethylene glycol with a relative molecular mass of 8,000, polyethylene glycol with a relative molecular mass of 12,000, and polyethylene glycol with a relative molecular mass of 15,000. The mixtures of polyethylene glycols with different relative molecular masses listed above are only example s, and are not intended to limit the present disclosure. The ionic salt may comprise at least one of NaCl and $MgCl_2$. For example, in an example, the ionic salt is NaCl. In another example, the ionic salt is $MgCl_2$. In yet another example, the ionic salt comprises both NaCl and $MgCl_2$.

In the magnetic bead suspension reagent, the volume of the surfactant accounts for 0.5%~5% (for example, 0.5%, 2.75%, 5%, etc.) of the volume of the magnetic bead suspension reagent, the mass of the dehydrating agent accounts for 20%~30% (such as 20%, 25%, 30%, etc.) of the mass of the magnetic bead suspension reagent, and the molarity of the ionic salt in the magnetic bead suspension reagent is 1mol/L~5 mol/L (such as 1 mol/L, 3 mol/L, 5 mol/L, etc.). By optimizing the ratio of surfactant, dehydrating agent and ionic salt in the magnetic bead suspension reagent, the conformational transition of DNA/RNA can be effectively controlled and the charged density of DNA/RNA can be increased. As a result, more DNA/RNA in the sample solution are specifically adsorbed to the surface of the magnetic beads, reducing the demand for the amount of magnetic beads. Therefore, under the condition of equal or higher purification efficiency, the embodiment of the present disclosure effectively reduces the amount of magnetic beads by optimizing the ratio among the surfactant, dehydrating agent and ionic salt in the magnetic bead suspension reagent, thereby significantly reducing the cost. In an example, the volume of the surfactant accounts for 0.5% of the volume of the magnetic bead suspension reagent, the mass of the dehydrating agent accounts for 30% of the mass of the magnetic bead suspension reagent, and the molarity of ionic salts in the magnetic bead suspension reagent is 1.5 mol/L. Such a ratio among surfactant, dehydrating agent and ionic salt can further optimize the conformational transition of DNA/RNA and further increase the charged density of DNA/RNA, so that more DNA/RNA in the sample solution are specifically adsorbed to the surface of magnetic beads, further reducing the need for magnetic beads.

In some embodiments, the magnetic bead suspension reagent can also comprise a buffer solution whose solute is tris(hydroxymethyl)aminomethane hydrochloride (Tris-HCL), which can act as a buffer system for the whole suspension in the magnetic bead suspension reagent. The molarity of the buffer solution can be 0.1 mmol/L~10 mmol/L (e.g. 0.1 mmol/L, 5.05 mmol/L, 10 mmol/L, etc.), and the pH value can be 7.5~8.5 (e.g. 7.5, 8, 8.5, etc.).

In some embodiments, the magnetic bead suspension reagent may further comprise a stabilizing solution, the solute of the stabilizing solution is ethylenediaminetetraacetic acid (EDTA). When the magnetic bead suspension reagent is mixed with the sample solution comprising nucleic acids, EDTA can act as a stabilizer to keep the nucleic acids stable and prevent the nucleic acids from being digested by enzymes. The molarity of the stabilizing solution can be 0.5 mmol/L~20 mmol/L (for example, 0.5 mmol/L, 10.25 mmol/L, 20 mmol/L, etc.).

In some embodiments, the magnetic bead may be superparamagnetic bead. As mentioned above, the superparamagnetic bead is not magnetic in the absence of an external magnetic field, and is evenly suspended in the magnetic bead suspension reagent; when an external magnetic field is applied, the magnetic bead is magnetic. The superparamagnetic magnetic bead has a three-layer structure, the innermost layer is polystyrene, the intermediate layer is $Fe_3O_4$, and the outermost layer is a modified layer with carboxyl and/or silanol functional groups. The ratio of the mass of the intermediate layer $Fe_3O_4$ to the overall mass of the magnetic bead is greater than 70%, and the particle size of the magnetic bead is 50 nm~4.5 μm (such as 50 nm, 100 nm, 500 nm, 1 μm, 2.3 μm, 4.5 μm, etc.), the concentration of the magnetic beads in the magnetic bead suspension reagent is 1-10 mg/mL (e.g. 1 mg/mL, 5.5 mg/mL, 10 mg/mL, etc.). It should be noted that although the particle size of the magnetic bead is 50 nm~4.5 μm, in the same batch of magnetic bead suspension reagents, the difference in particle size of the magnetic beads is less than 10%.

In the magnetic bead suspension reagent provided in the embodiments of the present disclosure, the solvent may be water.

The magnetic bead suspension reagent provided by the embodiments of the present disclosure, by making the surfactant comprise both nonionic surfactant and anionic/cationic surfactant, not only the nonionic surfactant can be relied on to maintain the dispersion of magnetic beads, but also anionic/cationic surfactants can be relied on to promote the formation of "electric bridge", thereby promoting the adsorption efficiency of nucleic acids by magnetic beads. By cooperating the surfactant with the dehydrating agent (polyethylene glycol) with appropriate relative molecular mass, a better dehydration-bridge forming system can be formed, thereby further improving the adsorption efficiency of nucleic acids by magnetic beads and promoting the purification and sorting effect of nucleic acids. By optimizing the ratio of surfactant, dehydrating agent and ionic salt in the magnetic bead suspension reagent, the conformational transition of DNA/RNA can be effectively controlled and the charged density of DNA/RNA can be increased, so that more DNA/RNA in the sample solution can be specifically adsorbed to the surface of the magnetic beads, reducing the need for the amount of magnetic beads. Compared with similar products in the related art, the magnetic bead suspension reagent provided by the embodiments of the present disclosure is equivalent to or higher than the industry gold standard AMPure XP, and at the same time, reduces the amount of magnetic beads, and significantly reduces the cost.

Figure 2:
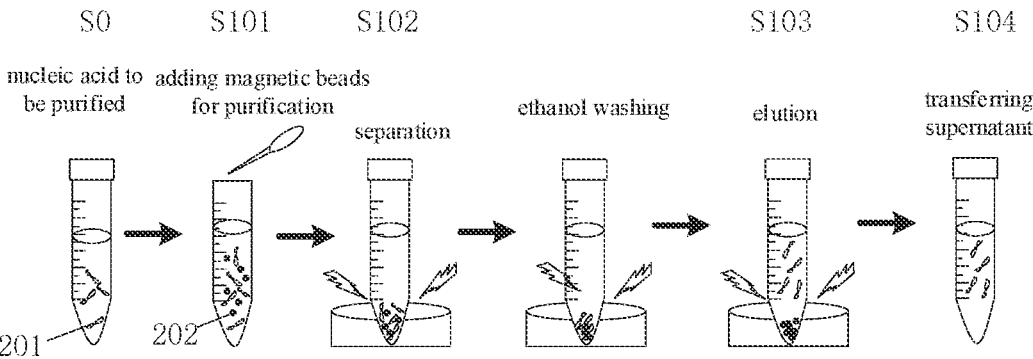
FIG. 2 illustrates a schematic diagram of the method of FIG. 1.

According to another aspect of the present disclosure, a method for purifying nucleic acids is provided. FIG. 1 shows a flowchart of the method 100, and FIG. 2 shows a schematic diagram of the method 100. The method 100 is described below with reference to FIGS. 1 and 2.

S101: mixing the magnetic bead suspension reagent described in any of the preceding embodiments with a sample solution comprising nucleic acids in a reaction tube to form a first mixed solution;

S102: placing the reaction tube accommodating the first mixed solution on a magnetic stand until the first mixed solution clear, and then removing a supernatant in the reaction tube;

S103: adding an eluent into the reaction tube to form a second mixed solution, placing the reaction tube accommodating the second mixed solution on the magnetic stand until the second mixed solution clear;

S104: collecting a supernatant in the reaction tube.

In some embodiments, the following sub-step may also be comprised between steps S102 and S103: adding an ethanol solution into the remaining solution in the reaction tube to form a third mixed solution, letting the third mixed solution stand until the third mixed solution clear, and then removing the supernatant comprising the ethanol solution; repeating the above step at least once.

In some embodiments, step S103 may comprise the following sub-step: taking out the reaction tube from the magnetic stand, adding Te buffer solution into the reaction tube at a ratio of 2 times the volume of the sample solution to form the second mixed solution, and then placing the reaction tube accommodating the second mixed solution on the magnetic stand, letting the second mixed solution stand until the second mixed solution clear.

The specific operation process involved in steps S101-S104 in FIG. 1 and FIG. 2 is described below with a specific example.

Before step S101, the magnetic bead suspension reagent is sufficiently shaken to redisperse the magnetic beads in the magnetic bead suspension reagent, which is beneficial to uniformly adsorb nucleic acids in the next step S101.

Step S0 in FIG. 2 shows a sample solution comprising nucleic acids (DNA and/or RNA) 201 to be purified and impurities that are desired to be removed, such as proteins, enzymes, primer dimers, dNTPs, and the like. Nucleic acids can be lysed from cells or other substances by physical or chemical treatment methods in advance, and can be greatly amplified in quantity by PCR technology. The treatment process of nucleic acids is not repeated in the embodiments of the present disclosure. As shown, the sample solution is contained in a reaction tube which can be any suitable container (e.g., a centrifuge tube), as long as the reaction tube does not undergo any chemical reaction with the magnetic bead suspension reagent and the sample solution and can fit the magnetic stand.

S101: mixing the magnetic bead suspension reagent described in any of the preceding embodiments with the sample solution comprising nucleic acids in a reaction tube to form a first mixed solution.

Adding the magnetic bead suspension reagent into the reaction tube accommodating the sample solution comprising nucleic acids at a ratio of the volume of the magnetic bead suspension reagent to the volume of the sample solution of approximately 0.8 (for example, adding 16 μL magnetic bead suspension reagent to 20 μL sample solution), and pipetting 10 times with a pipette tip to mix the two solutions thoroughly to form the first mixed solution. Then, standing and incubating the first mixed solution for 5 minutes. As mentioned above, the magnetic bead suspension reagent comprises magnetic beads, dehydrating agent (polyethylene glycol), ionic salt (NaCl and/or MgCl$_2$), surfactant, and the like. In the first mixed solution, the nucleic acid is dehydrated in a relatively high concentration of dehydrating agent and ionic salt, and the molecular conformation is compressed from a line to a curled sphere, and a large number of negatively charged phosphate groups are exposed. The negatively charged phosphate group and the outermost carboxyl functional group of the magnetic bead (202 in FIG. 2) form an "electric bridge" under the action of Na$^+$ and/or Mg$^{2+}$, so that the nucleic acid is specifically adsorbed to the surface of the magnetic bead. Since there is no external magnetic field at this time, the magnetic beads to which the nucleic acids are adsorbed are uniformly dispersed in the first mixed solution.

S102: placing the reaction tube accommodating the first mixed solution on a magnetic stand until the first mixed solution clear, and then removing a supernatant in the reaction tube.

The incubated first mixed solution is placed on the magnetic stand and stands for a time. Magnets or other substances that can exert a magnetic force are usually arranged on the magnetic stand. Under the action of the magnetic field of the magnetic stand, the magnetic beads adsorbed with nucleic acids are magnetically adsorbed to the bottom of the reaction tube, so the nucleic acids are also brought to the bottom of the reaction tube. After standing for enough time to make the magnetic beads adsorbed with nucleic acids all move to the bottom of the reaction tube, the first mixed solution becomes clear, and the upper part of the reaction tube is the supernatant (comprising impurities (such as proteins, enzymes, primer-dimers, dNTPs, etc.), polyethylene glycol, ionic salts, solvents, etc.). Then, aspirating the supernatant from the reaction tube using a device (such as a pipette) to remove impurities as well as polyethylene glycol and ionic salts from the solution, taking care not to touch the magnetic beads that have been adsorbed to the bottom of the reaction tube.

Before step S103, it also comprises washing the remaining solution in the reaction tube. The specific steps can be as follows: adding 200 microliters of 80% ethanol solution into the reaction tube, incubating for seconds until the solution clear, and then removing the ethanol solution (being careful not to touch the magnetic beads at the bottom of the reaction tube). Since the magnetic beads are adsorbed to the bottom of the reaction tube, the ethanol solution can be removed by removing the upper supernatant. Repeat this step at least once, wait until the ethanol solution is removed for the last time, and wait for a period of time to make the ethanol to evaporate, until there is no obvious ethanol solution on the surface of the magnetic beads. After the treatment in step S102, the impurities, polyethylene glycol and ionic salts in the first mixed solution have been substantially removed, but there may still be a trace amount of residue remaining in the solution. In this step, by washing with ethanol, the trace amount of impurities, polyethylene glycol and ionic salts are dissolved in the ethanol solution and removed together with the ethanol solution, so that the impurities can be completely removed and the purification efficiency of nucleic acids can be improved. The removal of polyethylene glycol and ionic salts facilitates the hydration of nucleic acids in the next step S103.

S103: adding an eluent into the reaction tube to form a second mixed solution, and placing the reaction tube accommodating the second mixed solution on the magnetic stand until the second mixed solution clear.

Taking the reaction tube out from the magnetic stand, adding 2 times the original sample solution volume of TE buffer solution (including 10 mmol/L tris(hydroxymethyl) aminomethane hydrochloride (Tris-HCl, pH 8.0) and 1 mmol/L ethylenediaminetetraacetic acid (EDTA)) into the reaction tube to form a second mixed solution; pipetting 10 times with a pipette tip until it becomes a homogeneous solution, and incubating for 5 minutes. Since the reaction tube has been removed from the magnetic stand, there is no external magnetic field, and the magnetic beads adsorbed with nucleic acids are re-dispersed in the second mixed solution. The TE buffer solution is an aqueous solution. Since the dehydrating agent and ionic salts have been completely removed in the previous step, when the TE buffer solution is added to the reaction tube, the nucleic acid molecules can be quickly and fully hydrated. The ion interaction among nucleic acid molecule, magnetic bead, and Na$^+$ ion (and/or Mg$^{2+}$ ion) is quickly released, so that the nucleic acids are dissociated from the surface of the magnetic beads and dispersed in the second mixed solution. Then, placing the reaction tube back on the magnetic stand until the solution clear. At this time, under the action of the external magnetic field, the magnetic beads without adsorbing any nucleic acids are adsorbed to the bottom of the reaction tube, and the nucleic acids dissociated from magnetic beads are dispersed in the supernatant.

S104: collecting the supernatant in the reaction tube.

Using a device (such as a pipette) to remove the supernatant from the reaction tube and placing it in a storage container. Be careful not to touch the magnetic beads at the bottom of the reaction tube when removing the supernatant from the reaction tube. Since the nucleic acids are dispersed in the supernatant and impurities are no longer present in the supernatant, the purification of the nucleic acids is achieved.

Figure 3:
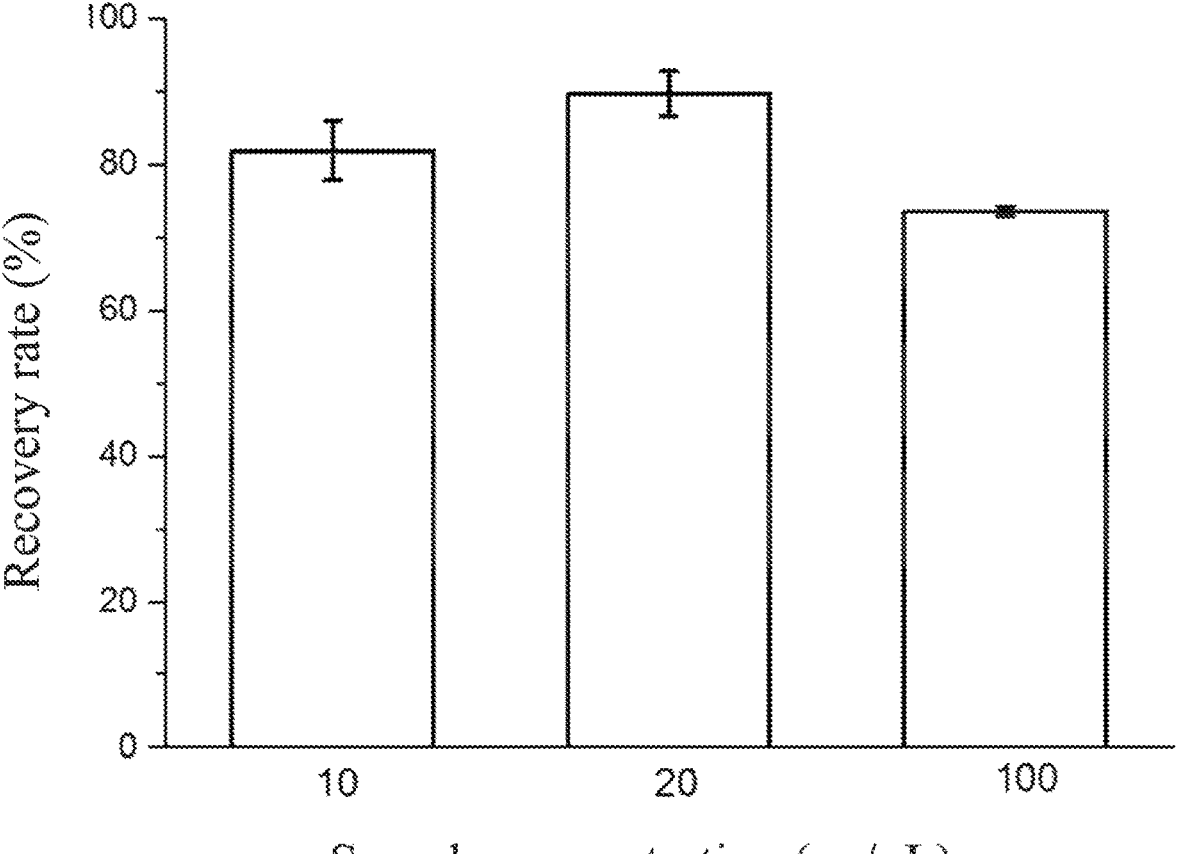
FIG. 3 illustrates the recovery rate of the nucleic acid which is purified by using the method of FIG. 1.

FIG. 3 shows the result of nucleic acid purification using the method 100 described above. As shown in FIG. 3, the abscissa is the sample concentration (ng/μL), that is, the nucleic acid concentration in the sample solution; the ordinate is the recovery rate of purified nucleic acids. As shown in the figure, when the sample concentration is 10 ng/μL, the recovery rate of purified nucleic acids is greater than 80%; when the sample concentration is 20 ng/μL, the recovery rate of purified nucleic acids is about 90%; when the sample concentration is 100 ng/μL, the recovery rate of purified nucleic acids is approximately 75%. This shows that by using the magnetic bead suspension reagent provided in the embodiments of the present disclosure to purify nucleic acids, the nucleic acids have a high recovery rate and are substantially not wasted.

Since the nucleic acids are purified by using the magnetic bead suspension reagent provided in the embodiments of the present disclosure, all the beneficial effects of the magnetic bead suspension reagent described in the previous embodiments are also possessed by this purification method. In addition, the use of magnetic bead suspension reagent to purify nucleic acid can process a larger dose of sample solution at a single time, which is beneficial to ensure the integrity of DNA/RNA molecules, improves the recovery rate of DNA/RNA molecules, reduces the need for magnetic beads consumption, and significantly reduces the cost.

Yet another aspect of the present disclosure provides a method for sorting nucleic acids. FIG. 4 shows a flowchart of the method 200, and the method 200 comprises the following steps:

S201: mixing the magnetic bead suspension reagent described in any of the preceding embodiments with a sample solution comprising nucleic acids in a first reaction tube to form a first mixed solution;

S202: placing the first reaction tube accommodating the first mixed solution on a magnetic stand until the first mixed solution clear, and then transferring a supernatant in the first reaction tube into the second reaction tube;

S203: mixing the magnetic bead suspension reagent described in any of the preceding embodiments with the supernatant in the second reaction tube to form a second mixed solution;

S204: placing the second reaction tube accommodating the second mixed solution on the magnetic stand until the second mixed solution clear, and then removing a supernatant in the second reaction tube;

S205: adding an eluent into the second reaction tube to form a third mixed solution, placing the second reaction tube accommodating the third mixed solution on the magnetic stand until the third mixed solution clear;

S206: collecting the supernatant in the second reaction tube.

In some embodiments, step S202 may comprise the following sub-steps: placing the first reaction tube accommodating the first mixed solution on the magnetic stand and letting the first mixed solution stand until the first mixed solution clear, so that the magnetic beads move to the bottom of the first reaction tube and adsorb the nucleic acids with a first length, and then transferring the supernatant comprising the nucleic acids with a second length and the nucleic acids with a third length in the first reaction tube into the second reaction tube. Where the first length is greater than the second length and the third length.

In some embodiments, step S204 may comprise the following sub-steps: placing the second reaction tube accommodating the second mixed solution on the magnetic stand and letting the second mixed solution stand until the second mixed solution clear, so that the magnetic beads move to the bottom of the second reaction tube and adsorb the nucleic acids with the second length, and then removing the supernatant comprising the nucleic acids with the third length in the second reaction tube. Where the second length is greater than the third length.

In some embodiments, step S206 may comprise the following sub-step: collecting the supernatant in the second reaction tube to obtain the nucleic acids with the second length.

In some embodiments, washing the remaining solution in the second reaction tube may also be comprised between steps S204 and S205, and the specific operation steps may comprise: adding an ethanol solution into the remaining solution in the second reaction tube to form a fourth mixed solution, letting the fourth mixed solution stand until the fourth mixed solution clear, and then removing the supernatant comprising the ethanol solution; repeating the above steps at least once.

In some embodiments, step S205 may comprise the following sub-steps: taking out the second reaction tube from the magnetic stand, adding Te buffer solution into the second reaction tube at a ratio of 2 times the volume of the sample solution to form the third mixed solution, and then placing the second reaction tube accommodating the third mixed solution on the magnetic stand and letting the third mixed solution stand until the third mixed solution clear.

The specific operation process involved in steps S201-S206 in FIG. 4 is described below with a specific example.

Before step S201, the magnetic bead suspension reagent is sufficiently shaken so that the magnetic beads are redispersed in the magnetic bead suspension reagent, so as to facilitate the adsorption of nucleic acids in the next step S201.

S201: mixing the magnetic bead suspension reagent described in any of the preceding embodiments with a sample solution comprising nucleic acids in a first reaction tube to form a first mixed solution.

adding the magnetic bead suspension reagent described in the previous embodiments into the first reaction tube accommodating the sample solution comprising nucleic acids in an appropriate proportion, and pipetting the mixture 10 times with a pipette tip, and mixing the two solutions thoroughly to form a first mixed solution. Then, incubating the first mixed solution for 5 minutes. The sample solution comprises nucleic acids with different lengths (for example, nucleic acids with a first length, nucleic acids with a second length, and nucleic acids with a third length, where the first length>the second length>the third length). Because the longer the fragmentation of nucleic acids is, the more charged it is, so it will be adsorbed to the surface of the magnetic bead earlier. Therefore, when the magnetic bead suspension reagent is mixed with the sample solution comprising nucleic acids, the nucleic acids with the first length are dehydrated in a high concentration of dehydrating agent and ionic salts (e.g., NaCl and/or $MgCl_2$), the molecular conformation is compressed from line to curled sphere, and a large number of negatively charged phosphate groups are exposed. The negatively charged phosphate group and the carboxyl functional group on the outermost layer of the magnetic bead form an "electric bridge" under the action of $Na^+$ and/or $Mg^{2+}$ ions, so that the nucleic acids with the first length are specifically adsorbed to the surface of the magnetic bead. Whereas other shorter nucleic acid fragments (i.e. nucleic acids with the second length and nucleic acids with the third length) are not adsorbed to the surface of the magnetic bead.

S202: placing the first reaction tube accommodating the first mixed solution on a magnetic stand until the first mixed solution clear, and then transferring a supernatant in the first reaction tube into the second reaction tube.

The incubated first mixed solution is placed on the magnetic stand. Under the action of the magnetic field of the magnetic stand, the magnetic beads adsorbing the nucleic acids with the first length are magnetically adsorbed to the bottom of the first reaction tube, so the nucleic acids with the first length are also brought to the bottom of the first reaction tube. When the first mixed solution becomes clear, the magnetic beads and the nucleic acids with the first length adsorbed on the magnetic beads are located at the bottom of the first reaction tube, and the upper part of the reaction tube is the supernatant, and the supernatant comprises the nucleic acids with a shorter length, polyethylene glycol, ionic salts, and some impurities (such as proteins, enzymes, primer dimers, dNTPs, etc.), etc. Then, using a device (such as a pipette) to transfer the supernatant from the first reaction tube to the second reaction tube, taking care not to touch the magnetic beads that have been adsorbed to the bottom of the first reaction tube.

S203: mixing the magnetic bead suspension reagent described in any of the preceding embodiments with the supernatant in the second reaction tube to form a second mixed solution.

adding the magnetic bead suspension reagent described in the previous embodiments into the second reaction tube in an appropriate proportion, the second reaction tube comprises the supernatant after the treatment in step S202, and pipetting it 10 times with a pipette tip. The two solutions are mixed thoroughly to form a second mixed solution. Then, incubating the second mixed solution for 5 minutes. As mentioned above, the supernatant in step S202 comprises nucleic acids with the second length and nucleic acids with the third length. When the magnetic bead suspension reagent is mixed with the supernatant, the nucleic acids with the second length are first adsorbed to the surface of the magnetic beads, while the nucleic acids with the third length are not adsorbed to the surface of the magnetic beads. It should be noted that the concentration or dose of the magnetic bead suspension reagent used in this step S203 and the concentration or dose of the magnetic bead suspension reagent used in step S201 may be the same or different, and the specific concentration or dose is based on process design, the embodiment of the present disclosure does not specifically limit this.

S204: placing the second reaction tube accommodating the second mixed solution on the magnetic stand until the second mixed solution clear, and then removing the supernatant in the second reaction tube.

The incubated second mixed solution is placed on the magnetic stand. Under the action of the magnetic field of the magnetic stand, the magnetic beads adsorbing the nucleic acids with the second length are magnetically adsorbed to the bottom of the second reaction tube, so the nucleic acids with the second length are also brought to the bottom of the second reaction tube. When the second mixed solution becomes clear, the magnetic beads and the nucleic acids with the second length adsorbed on the magnetic beads are located at the bottom of the second reaction tube, and the upper part of the reaction tube is the supernatant, and the supernatant comprises the nucleic acids with the third length, polyethylene glycol, ionic salts, and some impurities (such as proteins, enzymes, primer dimers, dNTPs, etc.), etc. The supernatant is then aspirated from the second reaction tube using a device such as a pipette, which can be transferred, for example, to a third reaction tube. Be careful not to touch the magnetic beads that have been adsorbed to the bottom of the second reaction tube when the supernatant is aspirated. At this time, the nucleic acids with the second length are left in the second reaction tube, and the nucleic acids with the third length and impurities are transferred to the third reaction tube. Thus, while sorting of the nucleic acids with the second length is effected, purification thereof is also effected at the same time.

Before step S205, it also comprises washing the remaining solution in the second reaction tube. The specific operation steps may comprise: adding 200 microliters of 80% ethanol solution into the second reaction tube, and then incubating for 30 seconds to remove the ethanol solution (be careful not to touch the magnetic beads at the bottom of the second reaction tube). Since the magnetic beads are adsorbed to the bottom of the second reaction tube, the ethanol solution can be removed by removing the upper supernatant. Repeating this step at least once, waiting until the ethanol solution is removed for the last time, waiting for a period of time so as to evaporate the ethanol, until there is no obvious ethanol solution on the surface of the magnetic beads. After the processing in step S204, the impurities, polyethylene glycol and ionic salts in the second mixed solution have been substantially removed, but there may still be a trace amount of residue remaining in the solution. In this step, by washing with ethanol, the trace amount of impurities, polyethylene glycol and ionic salts are dissolved in the ethanol solution and removed together with the ethanol solution, so that the impurities can be completely removed and the purification efficiency of nucleic acids can be improved. Therefore, after this step, the nucleic acids with the second length in the second reaction tube are further purified. The removal of polyethylene glycol and ionic salts facilitates the hydration of nucleic acids in the next step S205.

S205: adding an eluent into the second reaction tube to form a third mixed solution, and placing the second reaction tube accommodating the third mixed solution on the magnetic stand until the third mixed solution clear.

Removing the second reaction tube from the magnetic stand, and adding Te buffer solution (comprising 10 mmol/L tris(hydroxymethyl)aminomethane hydrochloride (Tris-HCl, pH 8.0) and 1 mmol/L ethylenediaminetetraacetic acid (EDTA)) to form a third mixed solution, pipetting 10 times with a pipette tip until it becomes a homogeneous solution, and incubating for 5 minutes. Since the second reaction tube has been removed from the magnetic stand, there is no external magnetic field, and the magnetic beads adsorbing the nucleic acids with the second length are re-dispersed in the third mixed solution. The Te buffer solution is an aqueous solution. Since the dehydrating agent and ionic salts have been completely removed in the previous step, when the Te buffer solution is added into the second reaction tube, the nucleic acid molecules with the second length are quickly and fully hydrated, so that the ionic interaction among the nucleic acids with the second length, the magnetic beads, $Na^+$ ions (and/or $Mg^{2+}$ ions) is quickly released, such that the nucleic acids with the second length are dissociated from the surface of the magnetic beads and dispersed in the third mixed solution. The second reaction tube is then placed back on the magnetic stand until the solution clear. At this time, under the action of an external magnetic field, the magnetic beads that do not adsorb any nucleic acid are adsorbed to the bottom of the second reaction tube, and the nucleic acids with the second length dissociated from the magnetic beads are dispersed in the supernatant.

S206: collecting the supernatant in the second reaction tube.

Using a device (such as a pipette) to take out the supernatant in the second reaction tube and placing it in a storage container. Be careful not to take out the magnetic beads at the bottom of the second reaction tube when taking out the supernatant in the second reaction tube. Since the nucleic acids with the second length are dispersed in the supernatant, sorting of the target nucleic acids is achieved.

In short, when using the magnetic bead suspension reagent to sort nucleic acid fragments, after the magnetic bead suspension reagent is added to the first reaction tube, the magnetic beads first bind to the nucleic acids with the large fragments (that is, nucleic acids with the first length) in the sample solution. The nucleic acids with the large fragments are left in the first reaction tube, and the nucleic acids with the shorter fragments are transferred into the second reaction tube together with the supernatant. After the magnetic bead suspension reagent is added into the second reaction tube, the magnetic beads bind to the larger fragments in the remaining volume in the system (i.e., bind to the nucleic acids with the second length), and the nucleic acids with the shorter fragments (i.e., the nucleic acids with the third length) are transferred to the third reaction tube together with the supernatant, and the nucleic acids with the second length are left in the second reaction tube.

Figure 5:
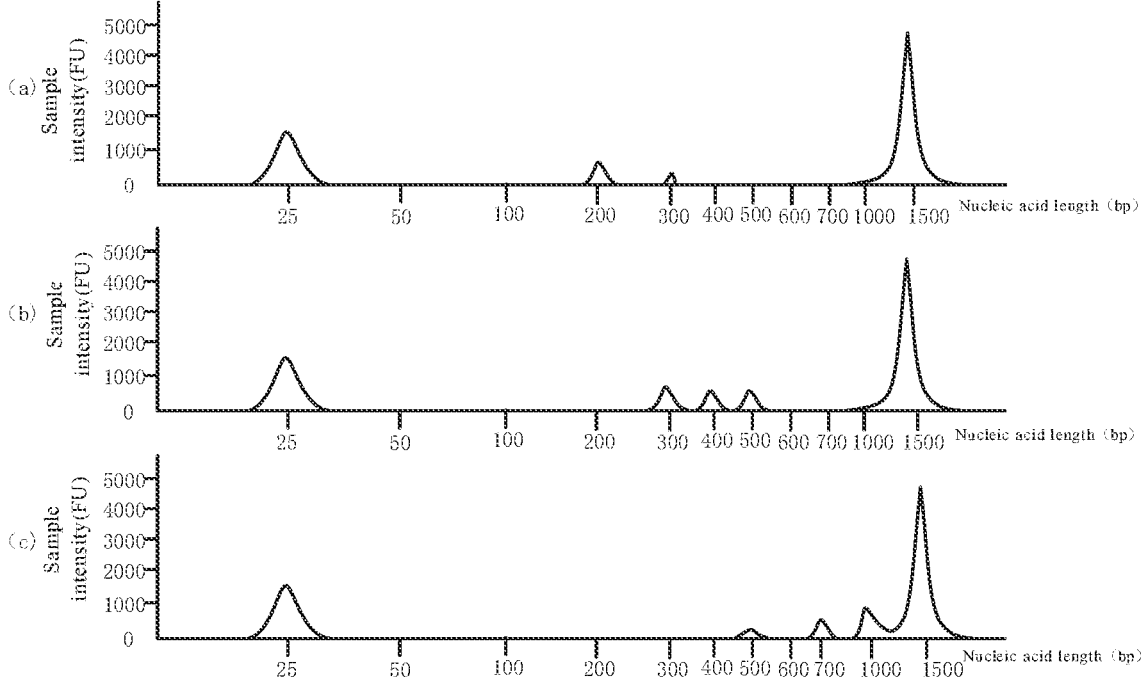
FIG. 5 illustrates the result of sorting nucleic acid using the method of FIG. 4.

FIG. 5 shows the result of sorting nucleic acid fragments using the method 200 described above. As shown in FIG. 5, the abscissa is the nucleic acid length (unit: bp), and the ordinate is the sample intensity (unit: FU), where the first peak (the corresponding abscissa is 25) and the last peak (the corresponding abscissa is 1500) in FIG. 5(*a*)-(*c*) are the reference values of the test system. In addition to the reference values, FIG. 5(*a*) shows two peaks whose abscissas are 200 and 300, respectively, representing the sorted nucleic acid fragments with fragment lengths of 200 bp and 300 bp, respectively (that is, nucleic acids with the third length). In addition to the reference values, FIG. 5(*b*) shows three peaks, whose abscissas are 300, 400, and 500, respectively, representing the sorted nucleic acid fragments with fragment lengths of 300 bp, 400 bp and 500 bp, respectively (i.e., nucleic acids with the second length). In addition to the reference values, FIG. 5(*c*) shows three peaks whose abscissas are 500, 700 and 1000, respectively, representing the sorted nucleic acid fragments with fragment lengths of 500 bp, 700 bp, and 1000 bp, respectively (i.e., nucleic acids with the first length).

Since the nucleic acids are sorted by using the magnetic bead suspension reagent provided in the embodiments of the present disclosure, all the beneficial effects of the magnetic bead suspension reagent described in the previous embodiments are also available in this sorting method. In addition, using the magnetic bead suspension reagent provided in the embodiments of the present disclosure to accurately sort nucleic acid fragments with different lengths, compared with traditional agarose gel electrophoresis for fragment separation and then gel-cutting recovery, the processing time is greatly shortened, the processed sample volume is greatly increased, and a loss of a large amount of nucleic acids is avoided. In addition, the whole process is easy to operate, and the nucleic acid fragments are sorted and purified at the same time, which is beneficial to ensure the integrity of nucleic acid molecules, improves the recovery rate of nucleic acid molecules, and reduces the demand for the amount of magnetic beads, thereby significantly reducing the cost.

As those skilled in the art will understand, although the various steps of the methods of the present disclosure are depicted in the figures in a particular order, this does not require or imply that the steps must be performed in that particular order, unless the context clearly dictates otherwise. Additionally or alternatively, multiple steps may be combined into one step for execution, and/or one step may be decomposed into multiple steps for execution. Furthermore, other method steps may be inserted between the steps. The inserted steps may represent improvements to the method such as those described herein, or may be unrelated to the method. Also, a given step may not be fully completed before the next step begins.

In the description of the present disclosure, the orientations or positional relationships indicated by the terms "upper", "lower", "left", "right", etc. are based on the orientations or positional relationships shown in the accompanying drawings, and are only used for the convenience of describing the present disclosure. This disclosure is not required to be constructed and operated in a particular orientation and is therefore not to be construed as a limitation of the disclosure.

In the description of this specification, description with reference to the terms "one embodiment," "another embodiment," etc. means that a particular feature, structure, material, or characteristic described in connection with the embodiment is comprised in at least one embodiment of the present disclosure. In this specification, schematic representations of the above terms are not necessarily directed to the same embodiment or example. Furthermore, the particular features, structures, materials or characteristics described may be combined in any suitable manner in any one or more embodiments or examples. Furthermore, those skilled in the art may combine the different embodiments or examples described in this specification, as well as the features of the different embodiments or examples, without conflicting each other. In addition, it should be noted that in this specification, the terms "first" and "second" are only used for description purposes, and cannot be understood as indicating or implying relative importance or implicitly indicating the number of indicated technical features.

The present disclosure illustrates the process method of the present disclosure through the above-mentioned embodiments, but the present disclosure is not limited to the above-mentioned process steps, that is, it does not mean that the present disclosure must rely on the above-mentioned process steps to be implemented. Those skilled in the art should understand that, within the technical scope disclosed in the present disclosure, easily conceivable changes or substitutions, the equivalent substitution of the selected raw materials in the present disclosure, the addition of auxiliary components, the selection of specific methods, etc., should all be comprised within the protection scope of the present disclosure. Therefore, the protection scope of the present disclosure should be based on the protection scope of the claims.

The invention claimed is:

1. A magnetic bead suspension reagent comprising:

magnetic beads; and a mixed surfactant, wherein the mixed surfactant comprises a nonionic surfactant, an anionic surfactant, and a cationic surfactant, the nonionic surfactant, the anionic surfactant, and the cationic surfactant are present in the magnetic bead suspension reagent.

2. The magnetic bead suspension reagent according to claim 1, wherein a side chain of both the anionic surfactant and the cationic surfactant comprises a carbon chain, and a length of the carbon chain is greater than or equal to 10 carbon atoms and less than or equal to 20 carbon atoms.

3. The magnetic bead suspension reagent according to claim 2, wherein the mixed surfactant is selected from a group consisting of Tween 20, polyethylene glycol octyl phenyl ether, sodium dodecyl sulfate, octadecyl diester quaternary ammonium salt.

4. The magnetic bead suspension reagent according to claim 2, wherein the mixed surfactant comprises Tween 20, sodium dodecyl sulfate and octadecyl diester quaternary ammonium salt.

5. The magnetic bead suspension reagent according to claim 1, further comprising:
   a dehydrating agent; and
   an ionic salt,
   wherein a volume of the mixed surfactant accounts for 0.5%~5% of a volume of the magnetic bead suspension reagent, a mass of the dehydrating agent accounts for 20%~30% of a mass of the magnetic bead suspension reagent, and a molarity of the ionic salt in the magnetic bead suspension reagent is 1 mol/L~5 mol/L.

6. The magnetic bead suspension reagent according to claim 5,
   wherein the volume of the mixed surfactant accounts for 0.5% of the volume of the magnetic bead suspension reagent, the mass of the dehydrating agent accounts for 30% of the mass of the magnetic bead suspension reagent, and the molarity of the ionic salt in the magnetic bead suspension reagent is 1.5 mol/L.

7. The magnetic bead suspension reagent according to claim 5,
   wherein the dehydrating agent comprises polyethylene glycol with at least one relative molecular mass, and the relative molecular mass of the polyethylene glycol is in a range of 8000~15000.

8. The magnetic bead suspension reagent according to claim 5,
   wherein the ionic salt is selected from a group consisting of NaCl and $MgCl_2$.

9. The magnetic bead suspension reagent according to claim 1, further comprising:
   a buffer solution,
   wherein the buffer solution comprises tris(hydroxymethyl)aminomethane hydrochloride, and a molarity of the buffer solution is 0.1 mmol/L~10 mmol/L, and a pH value of the buffer solution is 7.5~8.5.

10. The magnetic bead suspension reagent according to claim 1, further comprising:
   a stabilizing solution,
   wherein the stabilizing solution comprises ethylene diamine tetraacetic acid, and a molarity of the stabilizing solution is 0.5 mmol/L~20 mmol/L.

11. The magnetic bead suspension reagent according to claim 1,
   wherein each of the magnetic beads is a superparamagnetic magnetic bead, and the superparamagnetic magnetic bead has a three-layer structure, an innermost layer of the three-layer structure is polystyrene, an intermediate layer of the three-layer structure is $Fe_3O_4$, and an outermost layer of the three-layer structure is a modified layer with carboxyl and/or silanol functional groups.

12. The magnetic bead suspension reagent according to claim 11,
   wherein a ratio of a mass of the intermediate layer of the superparamagnetic magnetic bead to a mass of the superparamagnetic magnetic bead is greater than 70%, and a particle size of the magnetic bead is 50 nm~4.5 μm, and a concentration of the magnetic beads in the magnetic bead suspension reagent is 1~10 mg/mL.

*     *     *     *     *